(12) United States Patent
Zuber

(10) Patent No.: US 7,975,318 B2
(45) Date of Patent: Jul. 12, 2011

(54) HEAD STRAP

(75) Inventor: Gerhard Zuber, Meckesheim (DE)

(73) Assignee: AKO Kunststoffe Alfred Kolb GmbH, Sinsheim-Hoffenheim (DE)

( * ) Notice: Subject to any disclaimer, the term of this patent is extended or adjusted under 35 U.S.C. 154(b) by 1118 days.

(21) Appl. No.: 11/788,230

(22) Filed: Apr. 19, 2007

(65) Prior Publication Data
US 2007/0250986 A1    Nov. 1, 2007

(30) Foreign Application Priority Data
Apr. 28, 2006  (DE) .................. 20 2006 007 041

(51) Int. Cl.
*A42B 1/22*    (2006.01)
(52) U.S. Cl. ................................. 2/417; 2/410
(58) Field of Classification Search ............... 2/410, 6.6, 2/416–421
See application file for complete search history.

(56) References Cited

U.S. PATENT DOCUMENTS

| | | | |
|---|---|---|---|
| RE20,790 E | | 7/1938 | Bowers |
| 2,205,741 A | * | 6/1940 | Bowers ............... 2/8.1 |
| 2,437,748 A | * | 3/1948 | Malcom ............... 2/183 |
| 2,763,006 A | | 9/1956 | Amundsen |
| 3,047,876 A | | 8/1962 | Malcom, Jr. |
| 3,075,201 A | | 1/1963 | Lindblom |
| 3,866,244 A | * | 2/1975 | Ruck ............... 2/8.1 |
| 4,051,555 A | * | 10/1977 | Daly ............... 2/412 |
| 4,675,919 A | * | 6/1987 | Heine et al. ............... 2/410 |
| 4,988,093 A | * | 1/1991 | Forrest et al. ............... 482/10 |
| 5,027,479 A | * | 7/1991 | Scheffczyk ............... 24/196 |
| 5,044,019 A | * | 9/1991 | Shewchenko et al. ............... 2/421 |
| 5,571,217 A | | 11/1996 | Del Bon et al. |
| 5,768,715 A | * | 6/1998 | Gregg et al. ............... 2/411 |
| 5,887,288 A | * | 3/1999 | Arney et al. ............... 2/421 |
| 5,896,586 A | * | 4/1999 | Freund ............... 2/418 |
| 6,341,382 B1 | * | 1/2002 | Ryvin et al. ............... 2/417 |
| 6,367,085 B1 | * | 4/2002 | Berg ............... 2/202 |
| 6,966,074 B2 | * | 11/2005 | Huh ............... 2/414 |
| 7,441,282 B2 | * | 10/2008 | Heine et al. ............... 2/418 |
| 2007/0050892 A1 | * | 3/2007 | Charles ............... 2/410 |

FOREIGN PATENT DOCUMENTS

| | | |
|---|---|---|
| DE | 1 882 091 U | 11/1963 |
| DE | 198 60 148 | 7/1999 |
| DE | 200 14 383 U1 | 1/2001 |
| JP | 2004 292 978 | 10/2004 |

OTHER PUBLICATIONS

German Search Report Aug. 6, 2006 (and translation of pertinent portion).

* cited by examiner

*Primary Examiner* — Shaun R Hurley
*Assistant Examiner* — Andrew W Sutton
(74) *Attorney, Agent, or Firm* — Collard & Roe, P.C.

(57) ABSTRACT

A head strap for helmets, particularly welders' helmets, is configured in three parts and can therefore be provided with a separate forehead band. The head strap offers the possibility of connecting the helmet with the head strap in resilient or fixed manner, and, in this connection, of displacing the helmet relative to the head strap and/or rotating it between defined positions. Additional convenient adjustment possibilities for the back-of-the-head band and the head band are also implemented.

23 Claims, 5 Drawing Sheets

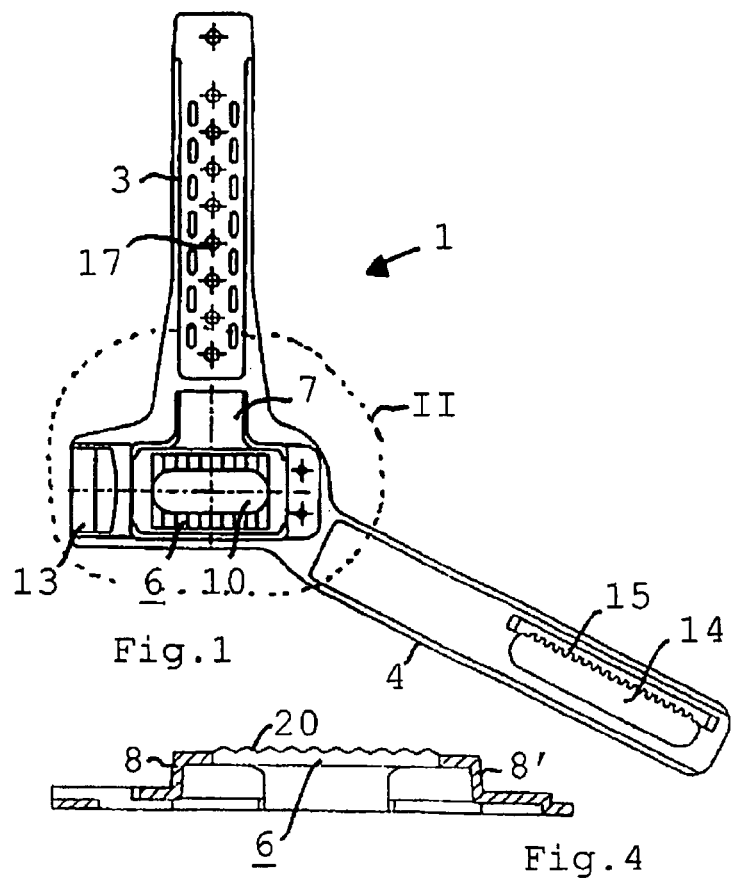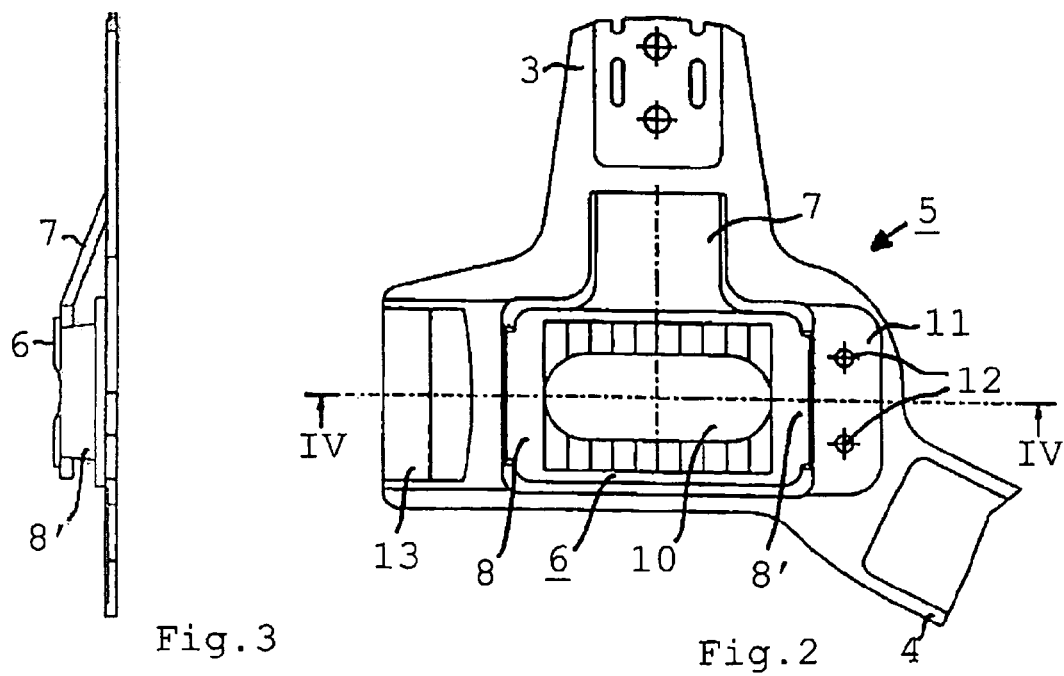

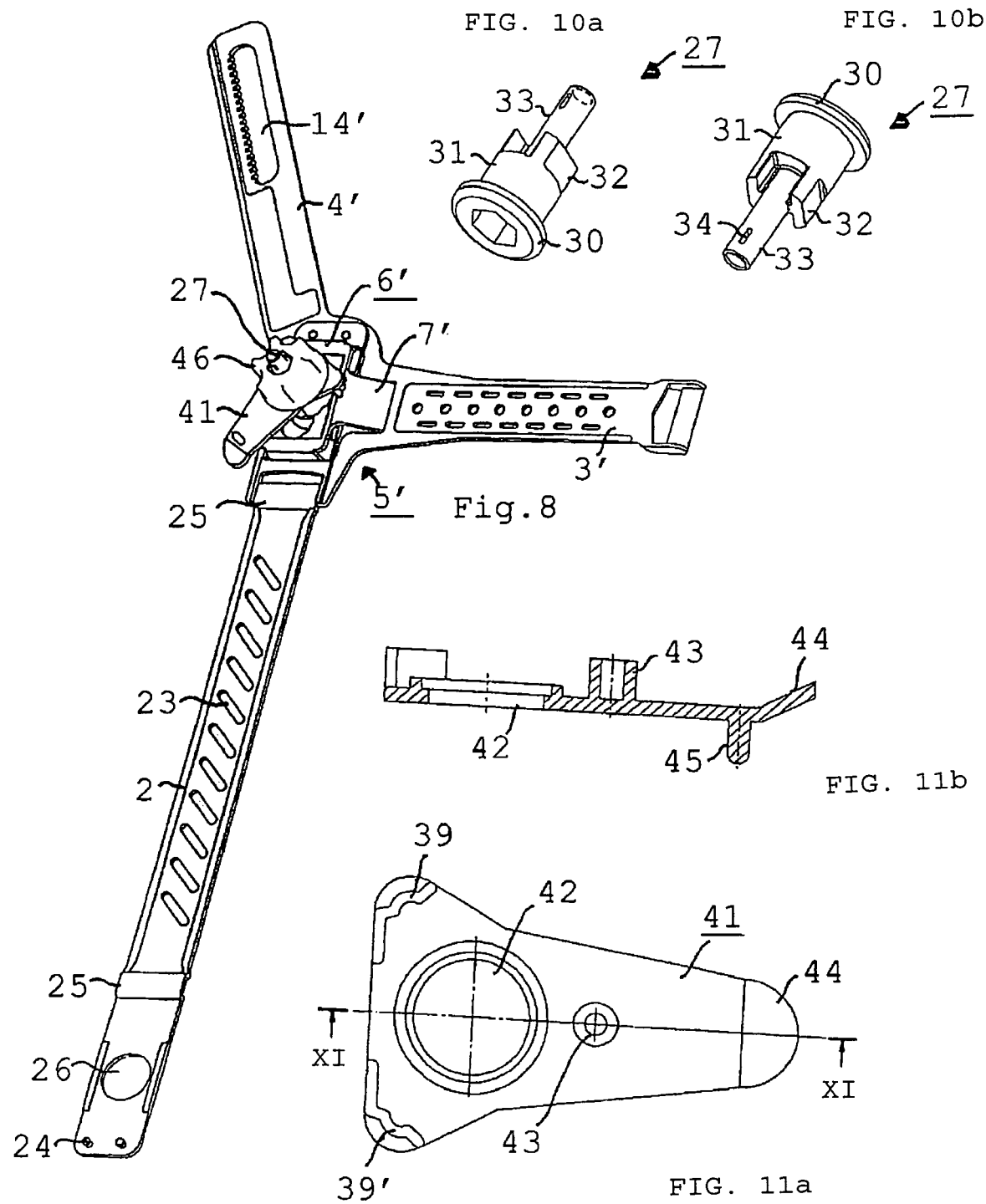

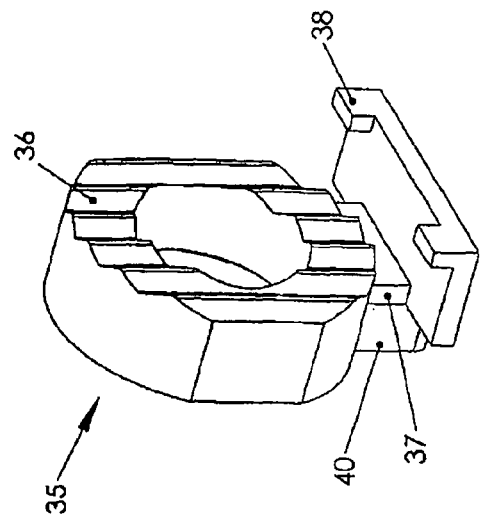
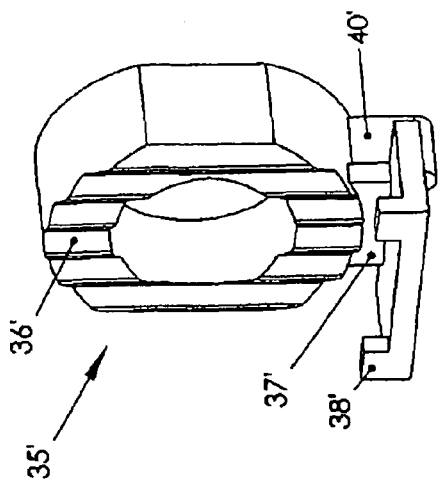
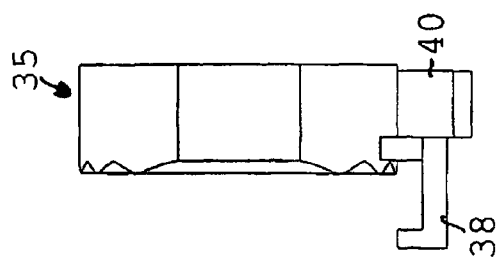
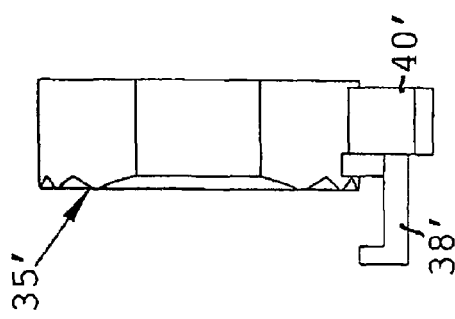
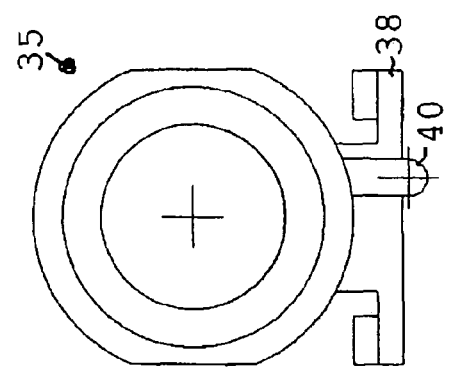
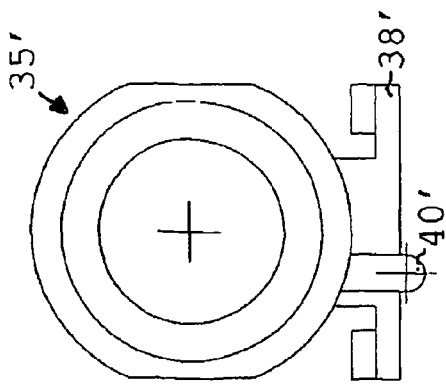

HEAD STRAP

CROSS REFERENCE TO RELATED APPLICATIONS

Applicant claims priority under 35 U.S.C. §119 of German Application No. 20 2006 007 041.9 filed Apr. 28, 2006.

BACKGROUND OF THE INVENTION

1. Field of the Invention

The present invention relates to a head strap for articulated connection with a helmet, particularly a welder's helmet. More particularly the head strap, when used as intended, surrounds the head of the helmet wearer with a forehead band and a back-of-the-head band, and in this connection, the cranium of the helmet wearer is surrounded by a head band, whereby the head strap is formed in three pieces, from a forehead band that can be separated, and a left and a right strap branching, each having a head band piece and a back-of-the-head band piece, which supplement one another to form the back-of-the-head band and the head band, when connected as intended, whereby additionally, the forehead band can be connected with the right and the left strap branching, as intended.

2. The Prior Art

A head strap with multiple parts is previously known from DE 200 14 383 U1, although primarily as a bicycle helmet. The disadvantage of the multi-part production of the head strap is balanced out, in this connection, by the advantage of the improved adjustment possibilities and the possibility of using different materials in the region of the head strap.

A head strap for a helmet, similarly composed of multiple parts, is also known from JP 2004-2 92 978 A.

Such head straps have been known for a long time in connection with construction site helmets, welders' helmets, or also bicycle helmets. In most embodiments, a helmet can be adapted to the individual head shape, as well as to the individual conditions of the user, by means of a head strap that is provided with many different kinds of adjustment possibilities. Furthermore, there is usually a space holder structured in some manner, between the head strap that is directly connected with the head of the user, and the helmet, in each instance. Furthermore, the helmets are usually connected with the corresponding head strap in articulated manner. The helmet is therefore generally adjustable relative to the head strap.

If necessary, the helmet can also be locked in certain positions. Thus, it is known from the sector of welders' helmets to configure the helmet essentially as a visor. The visor either can be flipped down or flipped up. When flipped down, the helmet completely covers the face relative to the work site, in other words on the front. When flipped up, the visor is raised to such an extent that the user's field of vision is cleared, to a great extent, in other words the visor is open.

Depending on the size of the tool used to produce the head straps, the head straps in question are produced in one piece or in multiple pieces. In the case of multi-piece embodiments, additional connection elements are generally required, in order to connect the individual pieces of the head strap with one another.

For better skin compatibility and for increased operating convenience, it is furthermore known to additionally cushion the forehead band region that rests against the forehead. It is also known to provide the forehead band region with ventilation slits or to provide material that is particularly skin-compatible, perspiration-absorbing, for the forehead band. Generally, however, the ease of operation and adjustment of the helmet is felt to be relatively unsatisfactory. The wearing comfort also appears to require improvement, at least for some applications.

SUMMARY OF THE INVENTION

It is an object of the invention, therefore, to provide an improved head strap, which particularly offers improved wearing comfort and operating convenience.

These and other objects are achieved by a head strap for articulated connection with a helmet, particularly a welder's helmet, in accordance with the invention. The head strap, when used as intended, surrounds the head of the helmet wearer with a forehead band and a back-of-the-head band, and in this connection, the cranium of the helmet is surrounded by a head band.

The head strap is formed in three pieces, from a forehead band that can be separated, and a left and a right strap branching. Each strap branching has a head band piece and a back-of-the-head band piece. The pieces supplement one another to form the back-of-the-head band and the head band when connected as intended.

Additionally, the forehead band can be connected with the right and the left strap branching as intended, and an articulated tab is cut out of the left and the right strap branching in an intersection region, in each instance, leaving at least one resilient crosspiece, and the head strap can be releasably connected with the helmet by way of these articulated tabs. This intersection region is disposed between the head band piece and the back-of-the-head band piece, in each instance. Advantageous embodiments of the invention are evident in accordance with the characteristics of the head strap discussed below.

Because the head strap according to the invention is configured in multiple parts, particularly in three parts, there is the possibility of producing the forehead strap separately, and of using materials that are rather soft for the forehead strap, in this regard. This flexibility is not possible when the head straps in question are produced in one piece, because rather hard materials, particularly plastics, are in demand in other regions of the head strap, for reasons of secure fastening or adjustment of the head strap. The possible production disadvantage, that the head strap cannot be produced in one piece, using an injection-molding method, is more than balanced out by the advantage of improved wearing comfort in the region of the forehead strap.

The multi-part configuration of the head strap furthermore makes it possible to better meet the needs of the individual user, in that further adaptations, for example to the head shape of the helmet wearer, are possible within the framework of connecting the individual parts. Aside from the forehead band, the head strap two strap branchings. Each of the strap branchings possesses an intersection region, which essentially represents the intersection point between the head band piece and the back-of-the-head band piece of the corresponding strap branching. In this region, an articulated tab is cut out of the solid material, whereby this articulated tab serves for a releasable connection with the helmet.

The releasable connection of helmet and head strap makes it possible to replace the head strap from time to time. In particular, however, the helmet can be individually attached relative to the head strap. Therefore the helmet can be individually attached relative to the user, in accordance with the needs of each user. The helmet can be positioned relative to the head of the wearer as desired. In this connection, the articulated tab can be designed entirely as desired, as a rigid or resilient, i.e. damped connection between helmet and head strap.

Because the articulated tab is cut out of the solid material of the strap branching, it is movable relative to the remainder of the strap branching. This feature offers a number of additional production advantages, for example in the production of the connection elements for connecting the head strap with the helmet.

In a specific and advantageous embodiment, the articulated tab can be connected with the remainder of the strap branching by way of a resilient crosspiece and at least one fixation crosspiece. In this embodiment, the articulated tab is fixed in place relative to the remainder of the head strap, so that an essentially static helmet fit relative to the head of the helmet wearer is obtained.

In an alternative embodiment, the fixation crosspieces are provided with at least one predetermined breaking point or at least one guide for a cutting element, for example a carpet knife, and can be cut off by these means, if necessary. The articulated tab remains connected with the remainder of the head strap only by way of the aforementioned resilient crosspiece, after the fixation crosspieces have been cut off.

Usually, however, the fixation crosspieces are already eliminated during the production of the resilient helmet connection, in other words they are not even formed onto the articulated tab, in the first place.

This arrangement results in an articulated—resilient—suspension of the helmet in this region. The intersection region of the strap branchings lies against the helmet wearer approximately in his/her temple region. As a result, many users find the arrangement when used as intended to be comfortable. This arrangement also provides a feeling of additional security, if the connection between helmet and head strap is made resilient, i.e. resiliently damped, in this region. There are also users who perceive this resilient connection as a source of unrest, and prefer a fixed fit. The variant with the fixation crosspieces that can be cut out, if necessary, makes it possible to serve both user interests with a single configuration of the head strap.

The articulated tab has a recess for a connection with the helmet. The use of an oblong hole as a recess in place of a simple insertion hole offers certain advantages. With this arrangement, depending on whether the helmet is attached in the front or rear region of the oblong hole, the helmet can be attached in this region farther forward or farther back relative to the head of the helmet wearer. Usually, the attachment is set not only in accordance with the individual interests of the user, but also in accordance with the individual head shape of the user, by means of using the adjustment possibilities formed by the oblong holes disposed on both sides. The use of oblong holes therefore represents an additional adjustment possibility of the helmet relative to the head of the helmet wearer, in each instance.

Fundamentally, of course, attention should be paid to setting the relative positioning of the connection elements in the two oblong holes of the strap branching, on the right and on the left, at least approximately the same, because otherwise, the helmet will sit crooked or rotated incorrectly. Therefore, it is practical to assign a marking to the oblong holes, in other words to each articulated tab, on the narrow side of the articulated tab, facing away from the resilient crosspiece, which marking makes it possible to attach the helmet at the same height on both sides of the head.

The articulated tab as such is provided with a profiling in the region surrounding this oblong hole, which profiling can be brought into engagement with a corresponding counter-contour of a connection element, to produce the connection with the helmet. The profiling furthermore serves to ensure precise positioning relative to the strap branchings. The profiling also makes sure, via the step-by-step adjustment possibilities that result from it, that the same relative position of the helmet with regard to the head of the user is set, with at least approximate precision.

In an advantageous embodiment, the profiling is provided as a wave profile with a 120° gear mechanism. This feature keeps the relative mobility of a connection element provided with a counter-contour from being unnecessarily difficult. This feature also allows easier movement of the connection element away from the articulated tab. Use of a gear mechanism that is less open, in other words a 90° gear mechanism, for example, creates the risk that the plastic parts of the connection elements will plastically deform readily. If such deformation occurs, the parts will be pressed against one another in such a manner that they can be released from one another only with difficulty. In this way, in the worst case, the adjustment possibility will be lost, to a great extent. It has therefore proven to be advantageous to provide a more open gear mechanism, for example a 120° gear mechanism.

In a specific embodiment, the connection between head strap and helmet can be imparted by way of a conventional screw/nut connection. In this connection, however, the connection can certainly take place with the interposition of additional connection elements.

In particular, it has proven advantageous to provide the screw/nut connection with a self-locking thread as security to prevent unscrewing. This arrangement can be implemented, for example, by carrying out the work with a changeable thread pitch. With this arrangement, before the connection is unscrewed to such an extent that there is a risk that the connection will break down into its individual parts and subsequently has to be assembled again, in complicated manner, a greater thread pitch may be provided. The user then feels increased resistance when loosening the connection, which must be overcome in order to completely release the connection. In this way, it is ensured that the screw/nut connection is released only if the user actually intends to do so, for example in order to replace individual connection elements. Unintentional opening of the connection is thereby prevented, to a great extent.

In an alternative embodiment, a slit or several slits can also be cut into the thread subsequently, in the aforementioned borderline region, in place of the changing thread pitch. Overcoming a slit worked into a thread in this manner is also connected with additional expenditure of force. Here again, the inhibition effect described above would be achieved, as intended.

In another further embodiment of the screw/nut connection, the connection screw of this connection is provided with a head piece and a thread section. In this embodiment, a round bolt is worked into the connection screw on the side facing the head piece. This round bolt in turn is provided with edge sections that lie diametrically opposite one another. These edge sections engage into corresponding recesses of the correspondingly pre-finished helmet, when assembled as intended. The edge sections therefore serve to prevent incorrect rotation of the helmet connected with the head strap.

As another element of the screw/nut connection, a positioning ring piece is provided on each side of the helmet, in each instance, which piece is set onto the articulated tab. This positioning ring piece is provided with the corresponding counter-contour to the profiling of the articulated tab on the surface facing the articulated tab. Of course, a 120° gear mechanism is preferred over a more sharply edged gear mechanism, for example 90°, in this case, as well. The reasons for this preference were explained previously.

Furthermore, a claw crosspiece is formed onto these positioning ring pieces, in each instance. This claw crosspiece engages over the articulated tab resting against the ring, and thereby first of all represents an attachment aid for the connection elements. This arrangement aids in attachment because it provides a first hold of the positioning ring piece relative to the articulated tab. Furthermore, these claw crosspieces, which engage over the articulated tabs, in each instance, ensure that when the connection is released, the articulated tab continues to be engaged, as intended. In this way, a guide exists during longitudinal movement of the connection screw in the oblong hole of the articulated tab, and, at the same time, offers security against incorrect rotation for the other connection elements relative to the connection screw, when the connection is tightened again.

As a further connection element, a contact lever is provided, which is provided with a bore for connecting with the connection screw mentioned above. The contact lever in question possesses at least two contact elements that project in the direction of the articulated tab, which elements limit the rotational mobility of the connection relative to the helmet. In the end result, the contact elements also represent rotation limitations for the helmet relative to the head strap, i.e. to the head of the wearer. For example, a visor function having at least two end positions—visor open, visor closed—can be implemented by way of the said contact elements.

Attachment elements that correspond with the forehead band are provided on both sides of the recess for forming the articulated tab. In a specific embodiment, these elements are a crosswise crosspiece for forming a strap tab, and a holder crosspiece, preferably configured in reinforced form, having corresponding holder holes. The holder holes can be connected with corresponding projecting connection nubs of the forehead band, with a force fit.

Because the forehead band is connected with the two strap branchings only subsequently, it can be produced in a separate production step. The forehead band can therefore advantageously be produced from a soft material such as plastic. In the interests of good and durable attachment, as well as permanent function of the adjustment possibilities of the head strap, the other elements of the head strap, which rest against regions of the head having less sensory activity, are produced from a harder plastic.

In the region of the face ends of the forehead band, the forehead band has projecting holder nubs, in order to be connected with corresponding holder holes of the strap branchings.

Furthermore, a backset is worked into the forehead strap, in the face-side end region, crosswise to the longitudinal expanse of the forehead strap, in each instance, which backset is set back relative to the remaining surface of the forehead band. When the forehead band is assembled as intended, the crosswise crosspiece of the strap branching engages into this backset with at least approximate shape fit. As a result, the forehead band, together with the crosswise crosspiece, forms an at least approximately planar surface relative to the head of the wearer. In this way, uncomfortable pressure points for the user are avoided in this region.

The two strap branchings are connected with one another not only by means of the forehead band, but also by means of the head band pieces. For this purpose, the head band pieces have connection elements that are complementary to one another, which can be supplemented, if necessary using additional intermediate pieces, to form the head band.

In a specific embodiment, the back-of-the-head band pieces are each provided with at least one oblong hole that extends in the longitudinal direction of the longitudinal expanse of the back-of-the-head band pieces. When assembled as intended, the back-of-the-head band pieces overlap, at least in the region of the oblong holes, in such a manner that the oblong holes also engage over one another, so that common connection elements engage through the two oblong holes in their overlap region, and the back-of-the-head band pieces are connected with one another in this region, in this manner, so that the back-of-the-head band pieces supplement one another to form the back-of-the-head band of the head strap, in this way. If necessary, the connection may be made with the insertion of additional intermediate pieces.

In an advantageous further embodiment, each oblong hole is provided with a respective toothed rack. One oblong hole has a top-side toothed rack, and the other oblong hole, in each instance, has a lower-side toothed rack, so that the two toothed racks supplement one another to form a gear mechanism, whereby a gear wheel that can be activated by means of a setting screw engages into this gear mechanism in such a manner that the two gear mechanisms, and with them the back-of-the-head band pieces are adjustable relative to one another, along their longitudinal expanse, by means of rotating the gear wheel.

In this connection, a force storage unit—for example a release spring—is assigned to the gear wheel, in such a manner that first, the spring force of this force storage unit must be overcome, in order to bring the gear wheel into engagement with the gear mechanism formed by the two toothed racks. This arrangement has the advantage that the adjustment of the back-of-the-head band pieces cannot be activated unintentionally, but rather only intentionally. The relative movement of the back-of-the-head band pieces relative to one another permits the helmet, i.e. the head strap of the helmet, to be adapted to the particular head circumference. In other words, the helmet can be attached more or less firmly, depending on the wishes of the user. Usually, this adjustment possibility is activated once by each user, at the beginning of use. During the course of further use, further adjustment is only required as an exception.

Another advantage of the release spring described is that the gear wheel is brought out of engagement with the toothed racks by means of the release spring, and moved into a release position. In this release position, however, the setting screw has a locking contour assigned to it. This locking contour interacts with the outside contour of the setting screw so that the setting screw hooks in in a defined position, so that in this way, additional security against unintentional rotation is produced.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, wherein similar reference characters denote similar elements throughout the several views:

FIG. 1 is a top view of a left strap branching;

FIG. 2 shows an intersection region of the left strap branching according to FIG. 1 in a detail view indicated in FIG. 1, also in a top view;

FIG. 3 is a side view of the intersection region shown in FIG. 2;

FIG. 4 is a sectional view of the intersection region shown according to the section designation in FIG. 2;

FIG. 8 is a perspective assembly drawing of a strap branching of the head strap with attached connection elements for connecting the head strap with a helmet;

FIGS. 9a-c and 9a'-c' show a left and a right positioning ring piece of the connection elements, in a rear, side, and perspective view, respectively;

FIGS. 10a-10b are perspective view of a connection screw of the connection elements;

FIGS. 11a and 11b are a top view and a cross-sectional view in accordance with the corresponding section designation in FIG. 11a, respectively, of a contact lever of the connection elements.

DETAILED DESCRIPTION OF PREFERRED EMBODIMENTS

Figure 5:
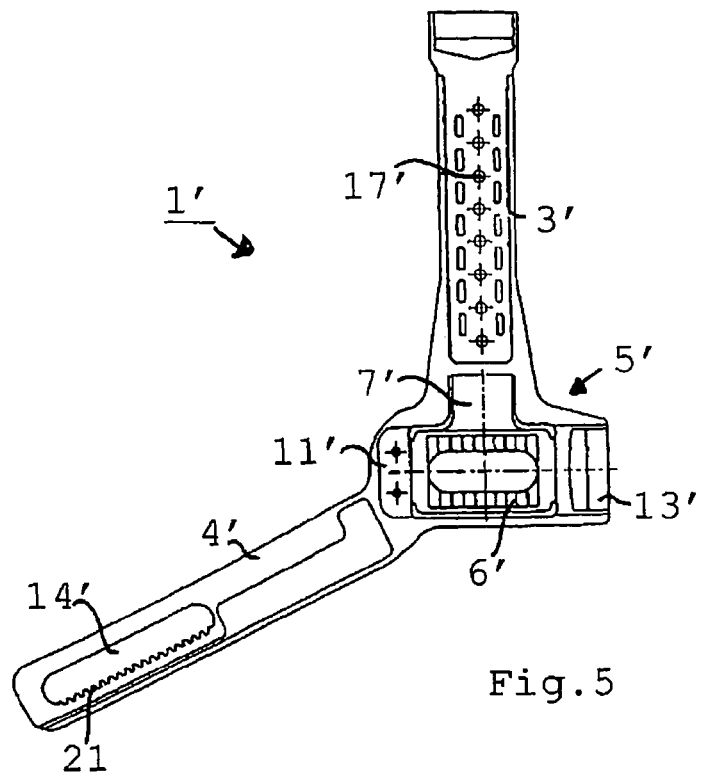
FIG. 5 is a tip view of a right strap branching of the head strap.
Figure 6:
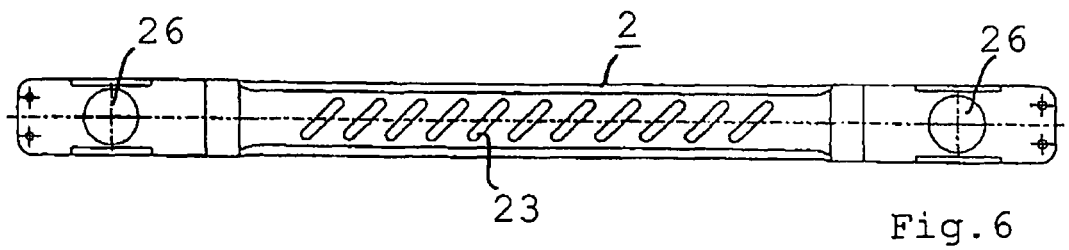
FIG. 6 is a top view of a forehead band of the head strap.
Figure 7:
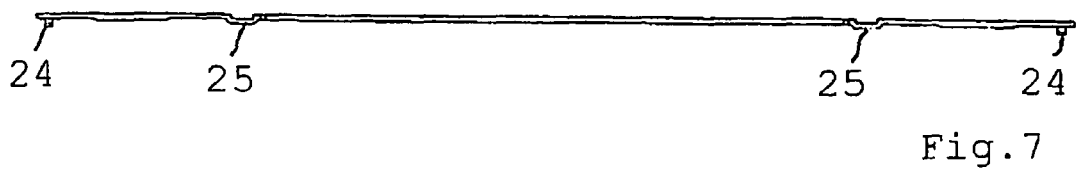
FIG. 7 is a side view of the forehead strap shown in FIG. 6.

Referring now in detail to the drawings, an exemplary embodiment of a head strap is shown, which is composed essentially of a left strap branching 1 according to FIG. 1 and a right strap branching 1' according to FIG. 5, as well as a forehead band 2 to be connected with the two strap branchings 1, 1', according to FIG. 6.

In the following, the individual parts of the head strap of the exemplary embodiment will be described, as follows:

Left strap branching 1 shown in FIG. 1 is composed essentially of a left head band piece 3 and a left back-of-the-head band piece 4, which are connected with one another by way of a common intersection region 5. Within this left intersection region 5, an articulated tab 6 is cut out, which is connected with left strap branching 1 by way of a resilient crosspiece 7. Articulated tab 6 is fixed in place relative to the back-of-the-head band piece, on both sides, with a fixation crosspiece 8, 8', in each instance, at a defined distance. Because articulated tab 6 forms the actual connection with the helmet, a fixed connection between helmet and head strap is formed by way of fixation crosspieces 8, 8'. If necessary, the articulated tab can also be formed on without fixation crosspieces 8, 8', or with only one fixation crosspiece 8 or 8'. Then this connection is configured to be more resilient or damped.

In a specific embodiment of the connection between helmet and head strap, articulated tab 6 is provided with an oblong hole 10. The use of an oblong hole 10 in place of a round bore makes it possible to select the relative positioning of the helmet relative to the head strap, i.e. to the skull of the helmet wearer, as a function of the circumstances of the individual case. On both sides of articulated tab 6, additional attachment elements are provided in intersection region 5, to connect left strap branching 1 with forehead strap 2. These attachment elements are a holder crosspiece 11 disposed in a depression, having two holder holes 12 into which corresponding connection nubs 24 of forehead band 2 can be clipped. On the other side of articulated tab 6, a crosswise crosspiece 13 is formed on, to form a strap tab.

Left back-of-the-head band piece 4 formed onto left strap branching 1 is provided with an oblong hole recess 14. This oblong hole recess 14 has an associated upper toothed rack 15. Left head band piece 3 is also provided with connection elements for interaction with right head band piece 3', with a suitable perforation 17.

The details already described in connection with FIG. 1 are shown once again, in greater detail, in FIGS. 2 and 3.

From FIG. 4, in particular, one can derive that oblong hole 10 of articulated tab 6 is provided with a wave profile 20 on its side facing away from the head of the wearer when worn as intended. This wave profile 20 serves for defined fixation of the connection elements relative to the longitudinal expanse of oblong hole 10, in a manner that will be explained in greater detail below, and thereby relative to the arrangement of the helmet relative to the head strap, i.e. to the head of the helmet wearer, in each instance.

According to the representation in FIG. 5, right strap branching 1' is also configured analogous to left strap branching 1, including a right intersection region 5' that connects a right head band piece 3' and a right back-of-the-head band piece 4'. Within common intersection region 5', an articulated tab 6' is cut out, which is connected with the right strap branching 1' by way of a resilient crosspiece 7'. Right head band piece 3' is also provided with connection elements for interaction with the left head band piece 3, with a suitable perforation 17'. In contrast to left strap branching 1, right back-of-the-head band piece 4' has a lower toothed rack 21, so that two toothed racks 15, 21 of oblong holes 14, 14' supplement one another to form a gear mechanism, the precise function of which will still be explained below, in connection with FIG. 13.

In the end result, left and right back-of-the-head band pieces 4, 4' therefore supplement one another to form the back-of-the-head band, whereby the two oblong holes of back-of-the-head band pieces 4, 4' overlap, in a manner not further shown, and hereby the two toothed racks 15, 21 form a common gear mechanism.

As a supplement, forehead band 2 is shown in a top view in FIG. 6. As is evident from the representation in FIG. 6, forehead band 2 can be seen separate from left and right strap branching 1, 1', and can be connected with these branchings, if necessary. This arrangement results, first of all, in the advantageous possibility of making forehead band 2 from a particularly soft material. Furthermore, forehead band 2 has ventilation slits 23 in the region that normally rests against the forehead.

For a connection with left and right strap branching 1, 1', forehead band 2 is provided with connection nubs 24 on both sides. Connection nubs 24 can be connected with holder holes 12 of holder crosspiece 11, 11' of left and right strap branching 1, 1'. In this connection, crosswise crosspiece 13, 13' engages into a setback 25 also formed onto the forehead band 2, so that forehead band 2 forms a planar surface relative to the head of the wearer in this region, if assembled as intended.

Furthermore, the forehead band has a round bore 26 in the region between setback 25 and connection nubs 24, in each instance, thereby facilitating the assembly of additional connection elements with articulated tab 6, 6' that makes contact in this region, in each instance, in a manner still to be clarified.

For this purpose, round bore 26 is in contact with oblong hole 10 of articulated tab 6 when forehead band 2 is assembled as intended. The additional connection elements, which are shown in a perspective representation in FIG. 8, in the assembled state, for example, engage through round bore 26 and oblong hole 10.

As is evident from this representation, the connection essentially is composed of a screw/nut connection that is formed with the interposition of a number of additional connection elements, which will be explained in greater detail below.

According to the representation in FIG. 8, a connection screw 27 is first inserted through round bore 26 of forehead band 2 and then oblong hole 10 of articulated tab 6. This connection screw 27 is shown in greater detail in FIGS. 10a-10b.

Connection screw 27 first of all possesses a head piece 30, which rests against the side of the oblong hole of the articulated tab, in each instance, that faces the head of the helmet wearer. This head piece 30 is followed by a round bolt 31 of connection screw 27, which ends with two edge sections 32 that lie diametrically opposite one another, on the side facing away from head piece 30. These edge sections 32 are followed by a threaded section 33, into which slits 34 that lie opposite one another are worked in the region facing away from head piece 30, to interrupt the thread. These slits 34 represent an unscrewing lock for the aforementioned screw/nut connection, because connection nut 46 that interacts with threaded section 33 can be unscrewed beyond the region of slits 34 only by exerting additional force.

The edge pieces themselves interact with a corresponding multi-edge recess of the helmet, in such a manner that the helmet is fixed in place so that it cannot be rotated incorrectly, while leaving the desired rotation function.

On the side of articulated tabs 6, 6' that faces away from head piece 30, when these are assembled with connection screw 27, as intended, a positioning ring piece 35, 35' is set onto connection screw 27, in each instance. These positioning ring pieces 35, 35' are shown in various views in FIGS. 9a-c and 9a'-c'. Positioning ring pieces 35, 35' have a counter-contour 36, 36' on the surface facing threaded or articulated tab 6, 6', in each instance, which interacts with wave profile 20 of threaded or articulated tab 6 in such a manner that when the screw/nut connection is fastened and closed, positioning ring pieces 35, 35' are clearly fixed in place relative to articulated tab 6. Then each counter-contour 36, 36' stands in engagement with the respective wave profile. Counter-contours 36, 36' are therefore provided with a 120° gear mechanism, in each instance, just like the respective wave profile, in order to allow easier release of the connection elements.

A claw crosspiece 38 is formed onto positioning ring piece 35, 35', in each instance, by way of a spacer crosspiece 37, 37'. In this connection, claw crosspiece 38 projects in the direction of articulated tab 6, 6', in each instance, and engages over the tab when the connection is closed. A crosswise crosspiece 40, 40' is formed onto spacer crosspiece 37, 37'. Crosswise crosspiece 40 extends essentially parallel to connection screw 27, in its longitudinal expanse, and serves as a stop for the incorrect rotation of a contact lever 41 that is connected with the helmet, in a manner that will still be clarified. As a comparison of FIGS. 9a and 9a' sufficiently makes clear, positioning ring pieces 35 and 35' are not the same pieces. Instead, they necessarily differ with regard to the positioning of crosswise crosspiece 40, 40' relative to these claw crosspieces 38, 38', depending on whether a stop is to be set on the right or the left side of the helmet, using crosswise crosspiece 40.

Contact lever 41 that has already been mentioned is shown in FIGS. 11a-11b, in a top view and in cross-section, respectively. Contact lever 41 possesses a cross-section that is at least essentially triangular. According to this representation, first of all, the contact lever also possesses a passage bore 42, so that it can be set onto connection screw 27. On the side facing positioning ring piece 35, two contact elements 39, 39' project in the direction of the positioning ring piece 35, which interact with crosswise piece 40 of positioning ring piece 35 in such a manner that in this way, the rotational mobility of contact lever 41 relative to positioning ring piece 35 is limited.

Furthermore, another contact pin 43 projects in the direction of positioning ring piece 35. Depending on the weight of the helmet, such a contact lever 41 can be mounted on the right strap branching 1' or on both strap branchings 1, 1'. During assembly on right strap branching 1', contact element 39 and contact pin 43 are in operation; during assembly on left strap branching 1, contact pin 43 and the other contact element 39' are in operation, accordingly.

The triangle side of contact lever 41 removed from passage bore 42 has an edged part 44 in the direction of positioning ring piece 35. This edged part 44 represents a handle piece for adjusting contact lever 41, which would otherwise lie flat against the side facing the helmet, in other words on the helmet interior.

On the surface that faces away from positioning ring piece 35 in the case of assembly as intended, in the transition region to edged part 44, a connection bolt 45 is furthermore formed on. Connection bolt 45 is additionally inserted into a corresponding hole of the helmet. If necessary, different holes can be provided in the helmet shell for this purpose, in order to allow different helmet positions relative to the head of the wearer.

From this arrangement, it follows, in turn, that with the limitation of the rotational mobility of contact lever 41, the rotational mobility of the helmet relative to the head strap and therefore to the helmet wearer is limited by contact elements 39, 39' and contact pin 43 of contact lever 41 and of positioning ring pieces 35, 35'.

The two stops 39 and 43 can correspond to the position—visor open, visor closed—in the case of a welder's helmet, for example.

Figure 12A:
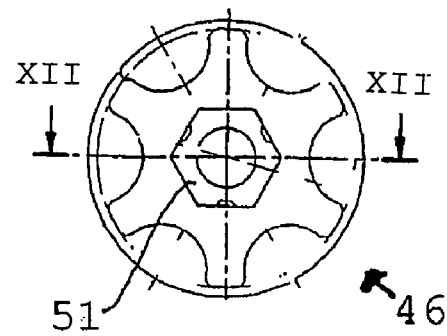
FIGS. 12a and 12b are a top view and a cross-sectional view in accordance with the corresponding section designation in FIG. 12a, respectively, of a connection nut of the connection elements.
Figure 12B:
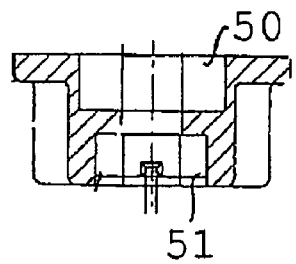

Finally, the connection is closed with connection nut 46 according to the representation in FIGS. 12a-12b. Connection nut 46 closes the screw/nut connection with connection screw 27. For this purpose, connection nut 46 has the handle of a wing nut, which can easily be held and rotated. In this connection, connection nut 46 first has to be connected with connection screw 27 by way of threaded section 33. When the connection is screwed closed for the first time, thread inhibition caused by slits 34 has to be overcome.

An insert nut is laid into a hexagonal socket 51, which is centrally disposed in the head of connection nut 46, to form the connection of connection screw 27 with connection nut 46. The use of a high-quality insert nut guarantees a permanently durable and renewable connection.

On the side of connection nut 46 facing connection screw 27, a bore 50 having an expanded inside diameter is provided. Expanded bore 50 centrally surrounds edge sections 32 when the connection is closed.

Figure 13:
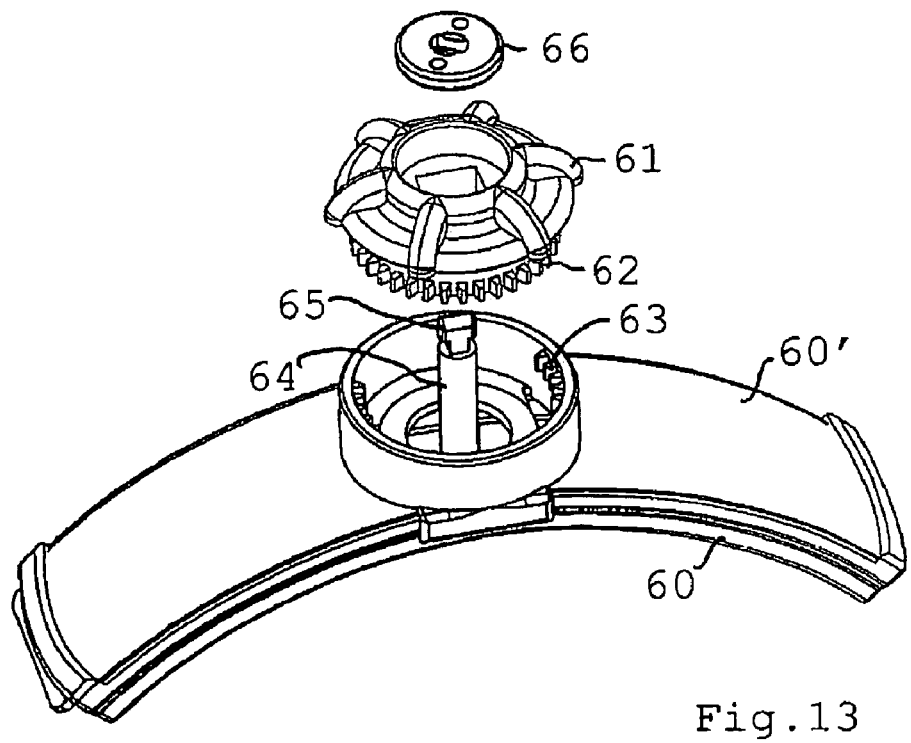
FIG. 13 is a detail representation for connecting the back-of-the-head band pieces, in a perspective exploded view.

FIG. 13 shows the adjustable connection of back-of-the-head band pieces 4, 4', over which a lower and upper cuff part 60, 60' engage, in the present case. As already mentioned, toothed racks 15, 21 of back-of-the-head band pieces 4, 4' supplement one another to form a gear mechanism. A gear wheel, not shown here, that can be moved by means of a setting screw 61 engages into this gear mechanism. In this way, a relative adjustment of the back-of-the-head band pieces 4, 4' relative to one another is brought about, whereby back-of-the-head band pieces 4, 4' are guided in a lower and upper cuff part 60, 60' in this connection, as intended. The helmet can be set narrower or wider by means of the adjustment of back-of-the-head band pieces 4, 4' relative to one another.

In order to bring this gear wheel into engagement with the gear mechanism, it is necessary to overcome the resistance of a release spring, also not shown in FIG. 13. However, this release spring also brings about release of a gear wheel 62 formed on setting screw 61, which comes into engagement with a gear crown 63 disposed concentric to setting screw 61, in order to thereby fix setting screw 61 in its position, in each instance.

In order to secure setting screw 61, in turn, against the release force of the release spring, a disk 66 is set onto a journal 64 that is formed on lower cuff part 60, and subsequently locked in place with a 90° rotation. The rotation of disk 66 has the result that a rectangular recess in disk 66, which corresponds to a locking crosspiece 65, which is formed on journal 64, no longer surrounds the journal but rather is disposed rotated relative to the journal, below the journal. Therefore, disk 66, and with it also setting screw 61, is secured.

Above, a specific exemplary embodiment of a head strap that can be composed from three elements, namely a left and a right strap branching 1, 1', as well as a forehead band 2, has therefore been described, whereby the head strap permits resilient or rigid attachment of the helmet to the head strap. In addition, the helmet can be displaced within a large adjustment range, in its position relative to the head of the helmet wearer, depending on the relative arrangement of the connection elements in oblong hole 10 in articulated tab 6.

Furthermore, defined stops in the sense of—visor open, visor closed—can be made possible by way of the contact elements of contact lever 41. Finally, the back-of-the-head band can be adapted to the head shape by means of a simple adjustment screw, by means of the gear mechanism formed by the two back-of-the-head band pieces 4, 4'. The head band pieces can also be supplemented to form a head band, in simple manner.

Above, a new type of head strap has therefore been described, which offers wearing convenience for helmets to be connected with this head strap that has never been seen before, by means of increased operational convenience and a plurality of adjustment possibilities.

Although only a few embodiments of the present invention have been shown and described, it is to be understood that many changes and modifications may be made thereunto without departing from the spirit and scope of the invention as defined in the appended claims.

What is claimed is:

1. A head strap for articulated connection with a helmet and for surrounding a helmet wearer's head comprising
   (a) a removable forehead band;
   (b) a left strap branching; and
   (c) a right strap branching;
   wherein each strap branching comprises a head band piece and a back-of-the-head band piece, said head band pieces and said back-of-the-head band pieces forming a head band and a back-of-the-head band, respectively;
   wherein said forehead band is connectable with said right strap branching and said left strap branching;
   wherein each strap branching has an articulated tab cut out from the strap to form in the strap branching at least one respective resilient crosspiece;
   wherein said articulated tabs are adapted to releasably connect with the helmet;
   wherein each intersection region is disposed between the head band piece and the back-of-the-head band piece of the respective strap branching; and
   wherein the head strap further comprises a respective crosswise crosspiece formed onto each strap branching for a releasable connection with the forehead band in a connection region that faces the forehead band next to the cut-out for the articulated tab for forming a forehead band tab, and a respective holder crosspiece formed on a side of the associated articulated tab that faces away from the forehead band, each holder crosspiece having at least one holder hole for corresponding connection nubs of the forehead band that project toward the holder hole.

2. The head strap according to claim 1, wherein each articulated tab is additionally connected with the respective strap branching by way of at least one fixation crosspiece.

3. The head strap according to claim 2, wherein the at least one fixation crosspiece is provided with at least one predetermined breaking point.

4. The head strap according to claim 2, wherein each articulated tab has a respective recess for connection to the helmet.

5. The head strap according to claim 4, wherein each articulated tab is provided with a marking for orienting the helmet relative to the helmet wearer's head.

6. The head strap according to claim 4, wherein each articulated tab is provided with a profiling engageable with a corresponding counter-counter of a connection element to form a connection with the helmet, at least in a region surrounding and directly adjacent to the recess, on a side facing away from the helmet wearer's head during use.

7. The head strap according to claim 6 wherein the helmet is connected with the articulated tabs of the right and left strap branching on each side of the helmet by way of a respective screw/nut connection.

8. The head strap according to claim 7, wherein each screw/nut connection is provided with a self-inhibiting thread for forming a respective anti-unscrewing lock of the connection.

9. The head strap according to claim 8, wherein each screw/nut connection comprises a connection screw having a head piece and a threaded section, a round bolt worked in between the threaded section and the head piece, and two edge sections that lie diametrically opposite one another worked into the bolt in an end region facing the threaded section, the edge sections being engageable with a correspondingly shaped recess of the helmet to form a shape fit.

10. The strap according to claim 1, wherein the forehead band is made of a soft material at least in sections.

11. The head strap according to claim 10, wherein a respective projecting connection nub is formed onto the forehead band in a region of each face-side end of the forehead band.

12. The head strap according to claim 10, wherein each crosswise crosspiece has a thickness and the forehead band has a longitudinal expanse and is provided with a set-back that runs crosswise to the longitudinal expanse of the forehead band on each side of the forehead band in a region that rests against the crosswise crosspiece of the strap tab of the strap branching when assembled, the set back being set back by a dimension, relative to a remainder portion of the forehead strap surface, that at least approximately corresponds to the thickness of the crosswise crosspiece.

13. The head strap according to claim 1, wherein each head band piece is provided with connection elements that are complementary to connection elements of another head band piece so that the head band pieces are connectable with one another to form a head band.

14. The head strap according to claim 1, wherein each back-of-the-head band piece is provided with connection elements that are complementary to connection elements of another back-of-the-head band piece so that the back-of-the-head band pieces are connectable with one another to form a back-of-the-head band.

15. The head strap according to claim 14, wherein each back-of-the-head band piece has a longitudinal direction and at least one oblong hole recess with a longitudinal expanse pointing toward the longitudinal direction of the respective back-of-the-head band piece, wherein the back-of-the-head band pieces, when assembled overlap at least in an overlap region of the respective oblong hole recess, and common connection elements pass through the overlapping oblong hole recesses of the back-of-the-head band pieces in the overlap region, the back-of-the-head band pieces thereby being releasably supplemented and connected to form the back-of-the-head band.

16. The head strap according to claim 15, wherein each oblong hole recess of the respective back-of-the-head band piece is provided with a toothed rack along a longitudinal side of the oblong hole recess, wherein a first oblong hole recess of a first back-of-the-head band piece has an upper toothed rack and a second oblong hole recess of a second back-of-the-head band piece has a lower toothed rack and each
   (b) a left strap branching; and
   (c) a right strap branching;
   wherein each strap branching comprises a head band piece and a back-of-the-head band piece, said head band pieces and said back-of-the-head band pieces forming a head band and a back-of-the-head band, respectively;
   wherein said forehead band is connectable with said right strap branching and said left strap branching;
   wherein each strap branching has an articulated tab cut out from the strap to form in the strap branching at least one respective resilient crosspiece;
   wherein said articulated tabs are adapted to releasably connect with the helmet;
   wherein each intersection region is disposed between the head band piece and the back-of-the-head band piece of the respective strap branching;
   wherein each articulated tab is additionally connected with the respective strap branching by way of at least one fixation crosspiece;
   wherein each articulated tab has a respective recess for connection to the helmet;
   wherein each articulated tab is provided with a profiling engageable with a corresponding counter-counter of a connection element to form a connection with the helmet, at least in a region surrounding and directly adjacent to the recess, on a side facing away from the helmet wearer's head during use;
   wherein the helmet is connected with the articulated tabs of the right and left strap branching on each side of the helmet by way of a respective screw/nut connection;
   wherein each screw/nut connection is provided with a self-inhibiting thread for forming a respective anti-unscrewing lock of the connection;
   wherein each screw/nut connection comprises a connection screw having a head piece and a threaded section, a round bolt worked in between the threaded section and the head piece, and two edge sections that lie diametrically opposite one another common connection element comprises a gear wheel that can be activated by means of a setting screw interacting with a gear mechanism formed by the upper and lower toothed racks when assembled so that the back-of-the-head band pieces are adjustable relative to one another, along the longitudinal expanse of the back-of-the-head piece by means of rotating the gear wheel.

17. A head strap for articulated connection with a helmet and for surrounding a helmet wearer's head comprising
   (a) a removable forehead band; worked into the bolt in an end region facing the threaded section, the edge sections being engageable with a correspondingly shaped recess of the helmet to form a shape fit; and
   wherein each screw/nut connection comprises a respective interposed contact level provided with a corresponding passage bore for the associated connection screw, each contact lever having at least two contact elements that project toward the articulated tabs and interact with an outside contour of a connection element or the articulated tabs so that each contact lever and the helmet connected with the contact lever so as to rotate with the contact lever is fixed in place in a relative position with regard to the head strap.

18. The head strap according to claim 17, wherein each contact lever is screwed together with a respective articulated tab by way of the screw/nut connection, with a positioning ring piece interposed between the contact lever and the tab, wherein an outside contour that interacts with the contact elements of the corresponding contact lever is formed onto the respective positioning ring piece.

19. The head strap according to claim 18, further comprising a respective claw crosspiece formed onto each positioning ring piece, said claw crosspiece engaging at least partially over the respective articulated tab that makes contact when assembled.

20. The head strap according to claim 18, wherein each profiling comprises a wave profile having a 120° gear mechanism, wherein each positioning ring piece is provided with a bore for putting the associated connection screw of the screw/nut connection through, and wherein a counter-contour that interacts with the wave profile is formed on the positioning ring piece in a region surrounding the bore.

21. A head strap for articulated connection with a helmet and for surrounding a helmet wearer's head comprising
   (a) a removable forehead band;
   (b) a left strap branching; and
   (c) a right strap branching;
   wherein each strap branching comprises a head band piece and a back-of-the-head band piece, said head band pieces and said back-of-the-head band pieces forming a head band and a back-of-the-head band, respectively;
   wherein said forehead band is connectable with said right strap branching and said left strap branching;
   wherein each strap branching has an articulated tab cut out from the strap to form in the strap branching at least one respective resilient crosspiece;
   wherein said articulated tabs are adapted to releasably connect with the helmet;
   wherein each intersection region is disposed between the head band piece and the back-of-the-head band piece of the respective strap branching;
   wherein each back-of-the-head band piece is provided with connection elements that are complementary to connection elements of another back-of-the-head band piece so that the back-of-the-head band pieces are connectable with one another to form a back-of-the-head band;
   wherein each back-of-the-head band piece has a longitudinal direction and at least one oblong hole recess with a longitudinal expanse pointing toward the longitudinal direction of the respective back-of-the-head band piece, wherein the back-of-the-head band pieces, when assembled overlap at least in an overlap region of the respective oblong hole recess, and common connection elements pass through the overlapping oblong hole recesses of the back-of-the-head band pieces in the overlap region, the back-of-the-head band pieces thereby being releasably supplemented and connected to form the back-of-the-head band;

wherein each oblong hole recess of the respective back-of-the-head band piece is provided with a toothed rack along a longitudinal side of the oblong hole recess, wherein a first oblong hole recess of a first back-of-the-head band piece has an upper toothed rack and a second oblong hole recess of a second back-of-the-head band piece has a lower toothed rack and each common connection element comprises a gear wheel that can be activated by means of a setting screw interacting with a gear mechanism formed by the upper and lower toothed racks when assembled so that the back-of-the-head band pieces are adjustable relative to one another, along the longitudinal expanse of the back-of-the-head piece by means of rotating the gear wheel; and wherein the head strap further comprises a respective force storage unit comprising a release spring acting on each gear wheel, each release spring having a spring force which must be overcome in order to bring the respective gear wheel into engagement with the gear mechanism of the back-of-the-head band pieces that overlap one another, at least in the region of the oblong holes.

22. The head strap according to claim 21, wherein the gear wheel and the setting screw that is connected with the gear wheel so as to rotate with the gear wheel is releasable via the release spring, the setting screw being provided with an additional gear wheel that comes into engagement with a gear crown associated with the setting screw in a released locking position.

23. A head strap for articulated connection with a helmet and for surrounding a helmet wearer's head comprising
    (a) a removable forehead band;
    (b) a left strap branching; and
    (c) a right strap branching;
    wherein each strap branching comprises a head band piece and a back-of-the-head band piece, said head band pieces and said back-of-the-head band pieces forming a head band and a back-of-the-head band, respectively;
    wherein said forehead band is connectable with said right strap branching and said left strap branching;
    wherein each strap branching has an articulated tab cut out from the strap to form in the strap branching at least one respective resilient crosspiece;
    wherein said articulated tabs are adapted to releasably connect with the helmet;
    wherein each intersection region is disposed between the head band piece and the back-of-the-head band piece of the respective strap branching;
    wherein each back-of-the-head band piece is provided with connection elements that are complementary to connection elements of another back-of-the-head band piece so that the back-of-the-head band pieces are connectable with one another to form a back-of-the-head band;
    wherein each back-of-the-head band piece has a longitudinal direction and at least one oblong hole recess with a longitudinal expanse pointing toward the longitudinal direction of the respective back-of-the-head band piece, wherein the back-of-the-head band pieces, when assembled overlap at least in an overlap region of the respective oblong hole recess, and common connection elements pass through the overlapping oblong hole recesses of the back-of-the-head band pieces in the overlap region, the back-of-the-head band pieces thereby being releasably supplemented and connected to form the back-of-the-head band;
    wherein each oblong hole recess of the respective back-of-the-head band piece is provided with a toothed rack along a longitudinal side of the oblong hole recess, wherein a first oblong hole recess of a first back-of-the-head band piece has an upper toothed rack and a second oblong hole recess of a second back-of-the-head band piece has a lower toothed rack and each common connection element comprises a gear wheel that can be activated by means of a setting screw interacting with a gear mechanism formed by the upper and lower toothed racks when assembled so that the back-of-the-head band pieces are adjustable relative to one another, along the longitudinal expanse of the back-of-the-head piece by means of rotating the gear wheel; and
    wherein each back-of-the-head band piece is provided with guide elements for another back-of-the-head band piece for possible contact in a region between the oblong hole recess and the intersection region of the respective strap branching.

* * * * *

UNITED STATES PATENT AND TRADEMARK OFFICE
CERTIFICATE OF CORRECTION

PATENT NO. : 7,975,318 B2
APPLICATION NO. : 11/788230
DATED : July 12, 2011
INVENTOR(S) : Zuber It is certified that error appears in the above-identified patent and that said Letters Patent is hereby corrected as shown below:

In particular, In Column 13, lines 20-57 (Lines 8-45 in Claim 16) please delete the following:

"(b) a left strap branching; and (c) a right strap branching;

wherein each strap branching comprises a head band piece and a back-of-the-head band piece, said head band pieces and said back-of-the-head band pieces forming a head band and a back-of-the-head band, respectively;
wherein said forehead band is connectable with said right strap branching and said left strap branching;
wherein each strap branching has an articulated tab cut out from the strap to form in the strap branching at least one respective resilient crosspiece;
wherein said articulated tabs are adapted to releasably connect with the helmet;
wherein each intersection region is disposed between the head band piece and the back-of-the-head band piece of the respective strap branching;
wherein each articulated tab is additionally connected with the respective strap branching by way of at least one fixation crosspiece;
wherein each articulated tab has a respective recess for connection to the helmet;
wherein each articulated tab is provided with a profiling engageable with a corresponding counter-counter of a connection element to form a connection with the helmet, at least in a region surrounding and directly adjacent to the recess, on a side facing away from the helmet wearer's head during use;
wherein the helmet is connected with the articulated tabs of the right and left strap branching on each side of the helmet by way of a respective screw/nut connection;
wherein each screw/nut connection is provided with a self-inhibiting thread for forming a respective anti-unscrewing lock of the connection;

Signed and Sealed this
Twenty-seventh Day of September, 2011

David J. Kappos
*Director of the United States Patent and Trademark Office*

CERTIFICATE OF CORRECTION (continued)
U.S. Pat. No. 7,975,318 B2 wherein each screw/nut connection comprises a connection screw having a head piece and a threaded section, a round bolt worked in between the threaded section and the head piece, and two edge sections that lie diametrically opposite one another".

In Column 14, line 1 (Line 3 of Claim 17) after the word "band;" please insert the following:
-- (b) a left strap branching; and (c) a right strap branching;

wherein each strap branching comprises a head band piece and a back-of-the-head band piece, said head band pieces and said back-of-the-head band pieces forming a head band and a back-of-the-head band, respectively;
wherein said forehead band is connectable with said right strap branching and said left strap branching;
wherein each strap branching has an articulated tab cut out from the strap to form in the strap branching at least one respective resilient crosspiece;
wherein said articulated tabs are adapted to releasably connect with the helmet;
wherein each intersection region is disposed between the head band piece and the back-of-the-head band piece of the respective strap branching;
wherein each articulated tab is additionally connected with the respective strap branching by way of at least one fixation crosspiece;
wherein each articulated tab has a respective recess for connection to the helmet;
wherein each articulated tab is provided with a profiling engageable with a corresponding counter-counter of a connection element to form a connection with the helmet, at least in a region surrounding and directly adjacent to the recess, on a side facing away from the helmet wearer's head during use;
wherein the helmet is connected with the articulated tabs of the right and left strap branching on each side of the helmet by way of a respective screw/nut connection;
wherein each screw/nut connection is provided with a self-inhibiting thread for forming a respective anti-unscrewing lock of the connection;
wherein each screw/nut connection comprises a connection screw having a head piece and a threaded section, a round bolt worked in between the threaded section and the head piece, and two edge sections that lie diametrically opposite one another --.